United States Patent
Vitushinsky et al.

(10) Patent No.: US 9,207,203 B2
(45) Date of Patent: Dec. 8, 2015

(54) TWO-DIMENSIONAL ELECTRON GAS SENSOR AND METHODS FOR MAKING AND USING THE SENSOR

(71) Applicant: Stichting IMEC Nederland, Eindhoven (NL)

(72) Inventors: Roman Vitushinsky, Vaals (NL); Peter Offermans, Eindhoven (NL); Mercedes Crego Calama, Geldrop-Mierlo (NL); Sywert Brongersma, Eindhoven (NL)

(73) Assignee: Stichting IMEC Nederland, Eindhoven (NL)

( * ) Notice: Subject to any disclaimer, the term of this patent is extended or adjusted under 35 U.S.C. 154(b) by 0 days.

(21) Appl. No.: 14/133,373

(22) Filed: Dec. 18, 2013

(65) Prior Publication Data

US 2014/0175516 A1    Jun. 26, 2014

(30) Foreign Application Priority Data

Dec. 21, 2012  (EP) ..................................... 12199289

(51) Int. Cl.
  *H01L 29/778* (2006.01)
  *G01N 27/414* (2006.01)
  *H01L 29/66* (2006.01)

(52) U.S. Cl.
  CPC ...... *G01N 27/4141* (2013.01); *H01L 29/66431* (2013.01); *H01L 29/778* (2013.01)

(58) Field of Classification Search
  CPC ............ H01L 29/2003; H01L 29/7787; H01L 29/66462; H01L 29/7786; H01L 29/66431; H01L 29/778; H01L 29/7782; H01L 29/13064
  See application file for complete search history.

(56) References Cited

U.S. PATENT DOCUMENTS

2008/0203431 A1  8/2008  Garcia et al.
2010/0065923 A1  3/2010  Charles et al.
(Continued)

FOREIGN PATENT DOCUMENTS

EP     2362459 A1    8/2011
GB     2294808 A     5/1996
WO  WO 03/014722 A1  2/2003

OTHER PUBLICATIONS

European Search Report for Application No. 12199289 dated May 17, 2013.
(Continued)

*Primary Examiner* — Selim Ahmed
*Assistant Examiner* — Wasiul Haider
(74) *Attorney, Agent, or Firm* — Knobbe, Martens, Olson & Bear LLP

(57) ABSTRACT

The disclosed technology generally relates to a sensor and methods for making and using the same, and more particularly relates to a sensor configured to sense the presence of at least one fluidum. In one aspect, a sensor for sensing a fluidum in a space adjoining the sensor comprises a two-dimensional electron gas (2DEG) layer stack. The sensor additionally comprises a gate lying adjacent to at least part of the 2DEG layer stack and configured to electrostatically control the electron density of a two-dimensional electron gas (2DEG) in the 2DEG layer stack. The sensor further comprises a source electrode contacting the 2DEG layer stack for electrically contacting the 2DEG. The 2DEG layer stack of the sensor comprises a contact surface contacting the space and provided to contact molecules of the fluidum which is desired to be detected, and the gate of the sensor comprises a doped semiconductor bottom layer of the 2DEG layer stack in electrical contact with at least one gate electrode, where the doped semiconductor bottom layer being located at a side of the 2DEG layer stack opposing the contact surface.

16 Claims, 1 Drawing Sheet

(56) References Cited

U.S. PATENT DOCUMENTS

| | | |
|---|---|---|
| 2012/0223370 A1 | 9/2012 | Zan et al. |
| 2012/0319169 A1* | 12/2012 | Van Hove .............. 257/194 |
| 2013/0240951 A1* | 9/2013 | Bedell et al. ............ 257/194 |
| 2013/0334061 A1* | 12/2013 | Offermans et al. ....... 205/775 |

OTHER PUBLICATIONS

Extended European Search Report for Application No. 12199289.5 dated May 27, 2013.

Nikolaides et al., "Silicon-on-Insulator Based Thin-Film Resistor for Chemical and Biological Sensor Applications," Chem Phys Chem, 2003, vol. 4, pp. 1104-1106.

Offermans et al., "Ultra-Sensitive $NO_2$ Detection with AlGaN/ GaN 2DEG Channels for Air Quality Monitoring," IEEE Sensors (2012) 3 pages.

Prokopuk et al., "Development of GaN-based Micro Chemical Sensor Nodes," IEEE Sensors (2005) pp. 199-202.

* cited by examiner

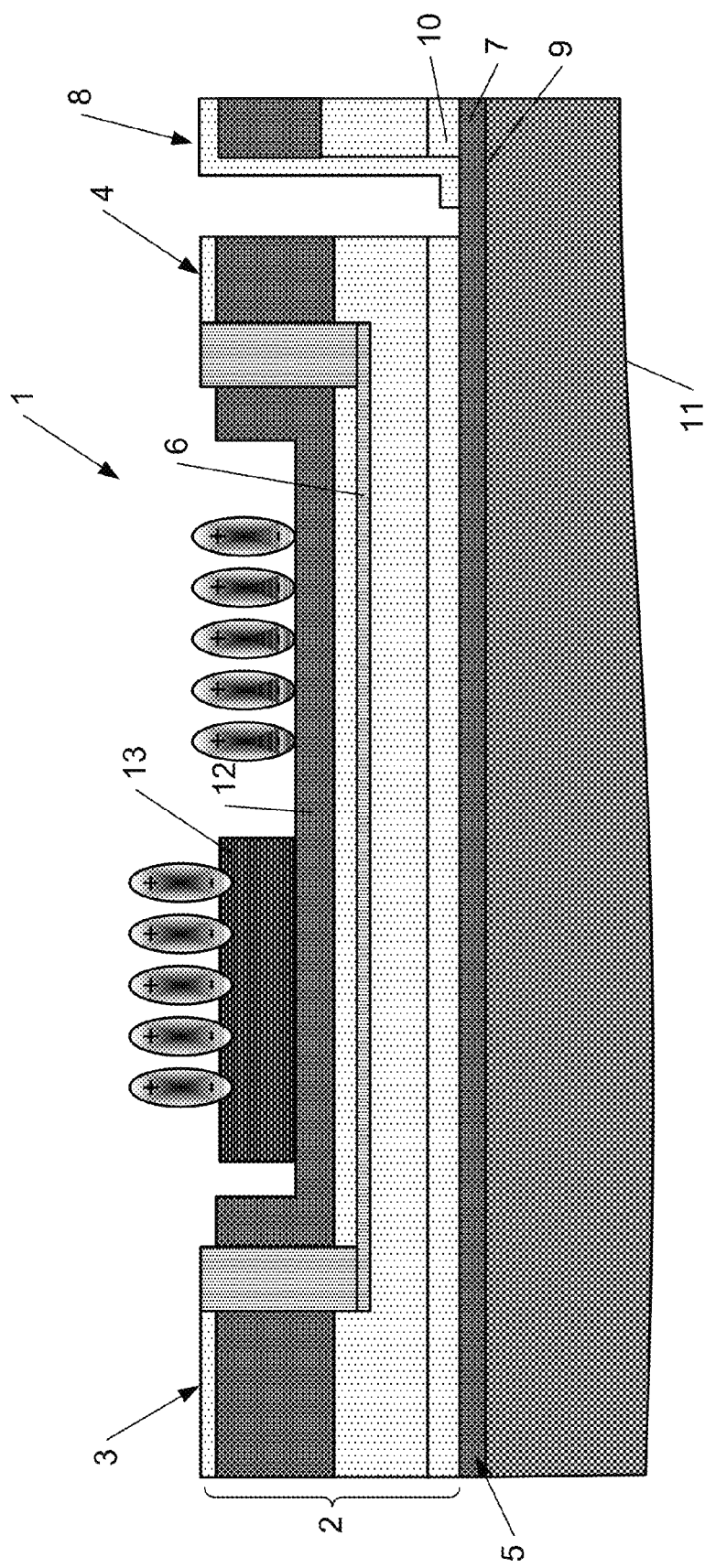

TWO-DIMENSIONAL ELECTRON GAS SENSOR AND METHODS FOR MAKING AND USING THE SENSOR

CROSS-REFERENCE TO RELATED APPLICATIONS

This application claims foreign priority to European patent application EP 12199289.5 filed on Dec. 21, 2012, the contents of which is incorporated by reference herein in its entirety.

BACKGROUND OF THE INVENTION

1. Field of the Invention

The disclosed technology generally relates to a sensor and methods for making and using the same, and more particularly relates to a sensor configured to sense the presence of at least one fluidum.

2. Description of the Related Technology

High electron mobility transistors (HEMT) utilize a two-dimensional electron gas (2DEG) formed at a heterojunction as conductive channels. HEMT devices find many applications due to the high mobility of the electrons in the 2DEG. For example, HEMT devices can be used as a sensor for sensing a fluidum. As used herein, a fluidum refers to a state of matter that is not a solid state, and includes gas and liquid states. The article "Development of GaN-based Micro Chemical Sensor Nodes," by Nicholas Prokopuk, Kyung-Ah Son, Thomas George and Jeong S. Moon, published in IEEE Sensors (2005), for example, describes a sensor for sensing the presence of at least one fluidum (a gas) in an adjoining space. The sensor comprises HEMT with a 2DEG (two-dimensional electron gas) layer stack comprising an AlGaN layer and a GaN layer. A gate overlays at least part of the 2DEG layer stack and electrostatically controls electron density of a 2DEG in the 2DEG layer stack. Molecules interfere with the contact surface of the 2DEG layer stack, in this case the surface of the AlGaN layer, and have an influence on the 2DEG in the 2DEG layer stack. The sensor also comprises a source and a drain electrode for contacting the 2DEG for measuring an electric characteristic of the 2DEG, more in particular the current between the source and the drain.

However, the gate of the sensor for controlling the electron density of the 2DEG must be kept small in order to provide a sufficiently large surface area in between the source and the drain above the 2DEG where fluidum, in this case vapor, molecules can alter an electric characteristic of the 2DEG, such as for example the current in between the source and the drain, for example by being adsorbed by the surface area in between the source and the drain above the 2DEG. As this limits the dimensions of the gate, which is provided for controlling the electron density of the 2DEG, the control of the electron density in the 2DEG is often insufficient.

Moreover, it has been found that the gate, even with limited dimensions, still reduces the area of the surface where the molecules can influence the 2DEG therefore limiting the sensitivity of the sensor, especially at very low concentrations of the molecules of the fluidum which is desired to be detected.

SUMMARY OF CERTAIN INVENTIVE ASPECTS

It is an object of the current disclosure to provide a sensor with which it is possible to improve the control of the electron density of the 2DEG while at the same time improving the sensitivity of the sensor.

According to an exemplary embodiment, the gate comprises a doped semiconductor bottom layer of the 2DEG layer stack in electrical contact with at least one gate electrode. The 2DEG layer stack comprises a contact surface contacting the space and provided to contact molecules of the fluidum which is desired to be detected. The doped semiconductor bottom layer is located at a side of the 2DEG layer stack opposing the contact surface and lies adjacent to at least part of the 2DEG layer stack for electrostatically controlling electron density of the 2DEG in the 2DEG layer stack.

It has been found that such a gate with a doped bottom layer forms a back-gate, which can be formed as an integrated back-gate, which allows a control of the electron density of the 2DEG while at the same time improving the sensitivity as the contact surface where the fluidum molecules, such as molecules of for example vapor, gas, liquid, can measurably alter the electric characteristics of the 2DEG is no longer hampered by the presence of the gate.

The change in electrical characteristic of the 2DEG can for example be detected and thus the presence of fluidum in the space can be detected, when a drain electrode is applied, the drain electrode contacting the 2DEG layer stack for electrically contacting the 2DEG, as a change in voltage across the source and the drain, a change in electrical current in between the source and the drain. Even when no drain is applied in the presence of a source electrode, or when the drain and the source are connected to a same voltage, or when one of the drain or source electrode is left unconnected, for example, a detected change in capacitance of the capacitor formed by the 2DEG and the doped semiconductor bottom layer can indicate that an electrical characteristic of the 2DEG has changed due to the presence of at least one molecule of the fluidum at the contact surface.

Moreover, it has been found that such doped semiconductor bottom layer can be made relatively easily. For example, by growing the 2DEG layer stack on a nucleation layer, for example an AlN nucleation layer, the nucleation layer being provided on a substrate, wherein during growth of the 2DEG layer stack, for example high temperature MOCVD as will be discussed later, atoms of the nucleation layer, diffuse into the substrate providing the doped semiconductor bottom layer to the 2DEG layer stack, wherein a gate electrode is provided in electrical contact with the doped semiconductor bottom layer, the doped semiconductor bottom layer forming a gate at a side of the 2DEG layer stack opposing the contact surface and thus forming an integrated back-gate.

Such diffusion of atoms from the nucleation layer into the substrate for forming the doped semiconductor bottom layer can especially be done by heating the substrate and the nucleation layer, for example during growth of the 2DEG layer stack on the nucleation layer. Such heating for example occurs when growing the 2DEG layers stack onto the nucleation layer using metalorganic vapor deposition (MOCVD). In such particular method the back-gate in other words is created during fabrication of the 2DEG layer stack such that after the 2DEG layer stack is formed usually no additional layers need to be created in order to create a back-gate, therefore making the creation of such back-gate relatively easy.

Moreover, as the gate is integrated in the substrate, part of the substrate, preferably the part of the substrate not comprising the doped semiconductor bottom layer can be removed afterwards, offering further possibilities for example for adding further layers.

Such a gate has been found to enable to control the conductivity of the 2DEG and/or the polarization of molecules gettered on the surface which can be used to improve the sensitivity of the sensor.

Moreover, it has been found that the presence of such gate can improve the recovery time of the sensor by electrostatic repulsion of the gettered molecules of the fluidum.

Moreover, the gate allows orienting dipoles at the surface leading to an increase of surface charge density which increases the interaction with the 2DEG further increasing the sensitivity of the sensor.

Also it has been found that the gate allows to improve the selectivity of the sensor towards certain fluida, such as liquids, gases, vapors, etc., as the gate potential for example allows to identify diverse surface adhered dipoles interacting with the gate field, for example applying a positive potential to the gate allows to attract dipoles having a negative surface while repelling dipoles having a positive surface.

Moreover, selectivity towards certain fluida, more in particular vapors and gases, can be improved by measuring the recovery time of the sensor as the recovery time of the sensor depends on for example the strength of the dipole at its surface.

According to exemplary embodiments of the current disclosure, the doped semiconductor bottom layer was doped with aluminum (Al) as it has been found that such doped semiconductor layer provides satisfying results. In such case, according to the method of the disclosure described above, the substrate would substantially be made of silicon which would then be doped, more specifically at the interface of the substrate with the nucleation layer, by atoms, for example the aluminum atoms, of the nucleation layer diffusing into the substrate, for example silicon substrate.

According to exemplary embodiments of the current disclosure, the 2DEG comprises a hetero-junction, preferably a GaN/AlGaN hetero junction in which case the contact surface preferably is the AlGaN layer.

According to exemplary embodiments of the current disclosure, the contact surface, for example the AlGaN layer, has a thickness of between 5 nm and 10 nm, preferably between 6 nm-7 nm as it has been found that at such relatively small thicknesses the interference of the atoms and/or molecules of the fluidum which is desired to be detected with the 2DEG can be improved leading to a sensor with an improved sensitivity.

According to exemplary embodiments of the current disclosure, the contact surface is provided with a functionalization layer for binding molecules of the fluidum, for example vapor or gas, which is desired to be detected. Such functionalization layer allows that molecules and/or atoms of the fluidum desired to be detected are bound or adsorbed. Such functionalization layer has been found to further increase the sensitivity and/or the selectivity of the sensor. Examples of such a functionalization layer comprise for example any one of and/or combinations of the following: polymers, redox-active molecules such as phthalocyanines, (metal) porphyrins, for example hemin ($C_{34}H_{32}N_4O_4FeCl$), biomolecules (DNA, receptors, antibodies, proteins), water molecules, for example forming a water vapor layer, for example a boundary surface water layer, etc.

The disclosure also relates to a method for making a sensor, for example the sensor according to the present disclosure, for sensing the presence of at least one fluidum, for example a vapor or gas, in a space adjoining the sensor, comprising a 2DEG (two-dimensional electron gas) layer stack, a gate lying adjacent to at least part of the 2DEG layer stack for electrostatically controlling electron density of a 2DEG in the 2DEG layer stack and a source electrode contacting the 2DEG layer stack for electrically contacting the 2DEG, by growing the 2DEG layer stack on a nucleation layer, the nucleation layer being provided on a substrate, wherein during growth of the 2DEG layer stack atoms of the nucleation layer diffuse into the substrate providing a doped semiconductor bottom layer to the 2DEG layer stack, wherein a gate electrode is provided in electrical contact with the doped semiconductor bottom layer, the doped semiconductor bottom layer forming the gate.

The obtained 2DEG layer stack comprises a contact surface contacting the space and provided to contact molecules of the fluidum, for example vapor or gas, which is desired to be detected. The doped semiconductor bottom layer is located at a side of the 2DEG layer stack opposing the contact surface and lies adjacent to at least part of the 2DEG layer stack.

In "Ultra-Sensitive $NO_2$ Detection with AlGaN/GaN 2DEG Channels for Air Quality Monitoring" by P. Offermans, R. Vitushinsky, M. Crego-Calama and S. H. Brongersma a similar method is described. However, although according to this method atoms of the nucleation layer will diffuse into the substrate when both are subjected to heat during the MOCVD process (here called metal-organic-vapor-phase epitaxy), no gate electrode is added.

Such diffusion of atoms from the nucleation layer into the substrate for forming the doped semiconductor bottom layer can especially be done by heating the substrate and the nucleation layer, for example during growth of the 2DEG layer stack on the nucleation layer. Such heating for example occurs when growing the 2DEG layers stack onto the nucleation layer using metalorganic vapor deposition (MOCVD). In such particular method the gate in other words is provided during fabrication of the 2DEG layer stack such that after the 2DEG layer stack is formed usually no additional layers need to be created in order to create the gate, therefore making the creation of such so-called back-gate relatively easy.

According to exemplary of the current disclosure, the nucleation layer is substantially made of AlN, especially when the 2DEG comprises a GaN/AlGaN hetero-junction with the contact surface being the AlGaN layer as in such case it has been found that a proper nucleation for the GaN layer is obtained.

The current disclosure also relates to the use of the sensor according to the present disclosure and/or made according to the method according to the present disclosure for sensing the presence of at least one fluidum, for example, as described above, by detecting a change in electric current between the source and the drain, a change in voltage across the source and the drain or by detecting a change in capacitance of the capacitor formed by the 2DEG and the doped semiconductor bottom layer. As a further example for sensing the presence of at least one fluidum, for example vapor or gas, when the material in between the 2DEG and the doped semiconductor bottom layer is a piezoelectric material, such as for example AlGaN, GaN, AlGaAs, GaAs, InGaN, AlN, etc., and when the 2DEG and the doped semiconductor bottom layer are used to periodically put a voltage across the 2DEG and the doped semiconductor bottom layer for periodically changing the shape of the piezoelectric material, by detecting a change in the resonance voltage at which the periodical change in shape of the piezoelectric material resonates, a change of the electric characteristic of the 2DEG can be detected and thus also the presence of the fluidum, for example vapor or gas, in the space.

According to exemplary embodiments of the current disclosure, the fluidum desired to be detected is a gas and comprises $NO_x$, with x for example being 1 or 2.

According to exemplary embodiments of the current disclosure, the sensor is most effectively used in a relative humidity of between 10%-90%.

BRIEF DESCRIPTION OF THE DRAWINGS

The disclosure will be further elucidated by means of the following description and the appended figures.

FIG. 1 shows a cross section of an embodiment of the sensor according to the present invention.

DETAILED DESCRIPTION OF CERTAIN ILLUSTRATIVE EMBODIMENTS

In the following detailed description, numerous specific details are set forth in order to provide a thorough understanding of the disclosure and how it may be practiced in particular embodiments. However, it will be understood that the present disclosure may be practiced without these specific details. In other instances, well-known methods, procedures and techniques have not been described in detail, so as not to obscure the present disclosure. While the present disclosure will be described with respect to particular embodiments and with reference to certain drawings, the disclosure is not limited hereto. The drawings included and described herein are schematic and are not limiting the scope of the disclosure. It is also noted that in the drawings, the size of some elements may be exaggerated and, therefore, not drawn to scale for illustrative purposes.

The present disclosure will be described with respect to particular embodiments and with reference to certain drawings but the disclosure is not limited thereto but only by the claims. The drawings described are only schematic and are non-limiting. In the drawings, the size of some of the elements may be exaggerated and not drawn on scale for illustrative purposes. The dimensions and the relative dimensions do not necessarily correspond to actual reductions to practice of the disclosure.

Furthermore, the terms first, second, third and the like in the description and in the claims, are used for distinguishing between similar elements and not necessarily for describing a sequential or chronological order. The terms are interchangeable under appropriate circumstances and the embodiments of the disclosure can operate in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the disclosure described herein are capable of operation in other orientations than described or illustrated herein.

The term "comprising", used in the claims, should not be interpreted as being restricted to the means listed thereafter; it does not exclude other elements or steps. It needs to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B.

FIG. 1 shows a cross section of the sensor 1 according to an exemplary embodiment.

The sensor 1 is suitable for sensing the presence of at least one fluidum in a space adjoining the sensor 1, more in particular adjoining a contact surface 12 of the sensor 1. The contact surface 12 contacts the space and is provided to contact molecules of the fluidum which is desired to be detected. The fluidum can be polar molecules. The fluidum may for example be any one or more of: $NO_x$, with x for example being 1 or 2, toluene, benzene, formaldehyde, etc. The fluidum can be in the form of a gas or a liquid.

By way of an example, some dipole molecules of a fluidum are represented at the contact surface 12 of the sensor 1.

The sensor 1 comprises a 2DEG (two-dimensional electron gas) layer stack 2. The 2DEG layer stack comprises a 2DEG 6. The 2DEG layer stack 2, as shown in FIG. 1, preferably comprises a hetero-junction. As materials for the hetero junction of the 2DEG layer stack, for example, typical III/V materials can be used such as for example GaAs/AlGaAs or III/N material, for example, AlGaN/GaN, which is chemically more stable and more biocompatible, in particular AlGaN/GaN, than III/V materials. Moreover, III/N material, in particular AlGaN/GaN, can be grown on conventional Si substrates, enabling lower cost end compatibility with conventional techniques. As shown in FIG. 1, preferably the AlGaN layer is positioned towards the space whereas the GaN layer is positioned away from to space with respect to the AlGaN layer. As shown on the right-hand side, the AlGaN layer forms the contact surface 12, although this is not critical for the invention as will be discussed later on. Usually, the thickness of the AlGaN layer in such configuration is between 5 nm-10 nm, preferably between 6 nm-7 nm, the thickness of the GaN layer being for example between 1-3 micron.

It has been found that a 2DEG allows high electron conductivity at room-temperature without increasing the electron mobility by external heating during operation, which can be beneficial, for example, in decreasing the overall power consumption of the sensor 1.

A gate 5 is provided lying adjacent to at least part of the 2DEG layer stack 2 for electrostatically controlling electron density of a 2DEG 6 in the 2DEG layer stack 2. The gate 5 comprises a doped semiconductor bottom layer 7. The doped semiconductor bottom layer 7 is part of the 2DEG layer stack and forms an integrated back-gate 9. As the gate 5 is provided adjacent to at least part of the 2DEG layer stack 2 and comprises the doped semiconductor bottom layer 7, which is part of the 2DEG layer stack, the gate 5 lies adjacent to the part of the 2DEG layer stack not being the doped semiconductor bottom layer 7.

The gate 9 is called integrated as it is formed during creation of the 2DEG layer stack as a part of the 2DEG layer stack as also will be explained later on. The gate 5 is called a back-gate 9 as it is not overlying the 2DEG layer stack 2 but instead is positioned underneath the 2DEG layer stack at a side of the 2DEG layer stack 2 opposing the contact surface 12.

The doped semiconductor bottom layer 7 of the 2DEG layer stack 2 is in electrical contact with at least one gate electrode 8. The gate electrode 8 is used for electrically controlling the back-gate 9 such that the electron density of the 2DEG 6 in the 2DEG layer stack 2 can be electrostatically controlled by applying a voltage to the gate electrode 8. The type of voltage can be determined by the person skilled in the art depending on, for example, the application of the sensor 1.

The gate electrode 8 shown in FIG. 1 is provided in the form of a layer of conductive material contacting the integrated back-gate 9. The conductive material can be any conductive material known the person skilled in the art such as for example silver, gold, copper, etc. depending on the desired properties of the sensor 1.

A source and a drain electrode 3, 4 contacting the 2DEG layer stack 2 for electrically contacting the 2DEG 6 are provided. As discussed above, although only embodiments are shown in which a drain is provided, the presence of the drain is not critical for the disclosure and can be omitted depending on the desired application of the sensor 1.

The sensor 1 can be provided on a substrate 11. The substrate 11 for example comprises silicon, although other materials are possible.

The doped semiconductor bottom layer 7 represents part of the substrate 11 doped with atoms from the nucleation layer 10. When for example a silicon substrate 11 is provided and for example the AlN nucleation layer 10 is provided, the doped semiconductor bottom layer 7 is created by doping of the substrate with Al-atoms of the nucleation layer 10, for example under influence of heat, for example during MOCVD.

However, the substrate 11 is not critical for the disclosure and the substrate 11 can also be omitted.

As shown on the left hand side of FIG. 1, the contact surface 12 can be provided with a functionalization layer 13 for binding molecules of the fluidum which is desired to be detected. In the configuration shown, the functionalization layer 13 is provided on top of the hetero-junction. The functionalization layer 13 can for example be a hemin layer.

Although FIG. 1 shows that the functionalization layer 13 is provided along a portion of the contact surface 12 adjoining the space, the functionalization layer 13 can also be provided along substantially the entire contact surface 12 to further improve sensitivity of the sensor 1. Application of the functionalization layer 13 can be determined in function of the desired application of the sensor 1 by the person skilled in the art.

The sensor 1 can be used for sensing the presence of at least one fluidum. Based on the sensed presence of the at least one fluidum further information can be gathered on pH, concentration of ions in solutions, etc.

To make a sensor as shown in FIG. 1 for sensing the presence of at least one fluidum, for example vapor or gas, the 2DEG layer stack 2 is grown on a nucleation layer 10. The nucleation layer 10 is provided on a substrate 11, for example a substrate comprising silicon as described above. During growth of the 2DEG layer stack 2 atoms of the nucleation layer 10 diffuse into the substrate 11 providing a doped semiconductor bottom layer 7 to the 2DEG layer stack 2. If a sensor is desired without all of the substrate 11 present, as described above, part of the substrate 11, for example the part of the substrate not comprising the doped semiconductor bottom layer 7, can be removed after creation of the doped semiconductor bottom layer 7.

A gate electrode 8 is provided in electrical contact with the doped semiconductor bottom layer 7, the doped semiconductor bottom layer 7 forming the integrated back-gate 9. As can be seen in FIG. 1, the gate electrode 8 is for example provided by removing part of the material of the 2DEG stack 2 up to the doped semiconductor bottom layer 7 after which a conductive layer is applied along the doped semiconductor bottom layer 7, along an upwards side delimiting the removed part of the 2DEG stack 2 and, preferably as shown in FIG. 1, along part of the surface of the 2DEG stack 2. The conductive layer forms the gate electrode 8.

The material of the nucleation layer is chosen in function of the 2DEG layer stack 2. For example, the nucleation layer is substantially made of AlN when a GaN/AlGaN hetero junction is used in the 2DEG layer stack 2 on a silicon substrate 11.

During growth of the 2DEG layer stack 2 on the nucleation layer 10, the substrate 11 and the nucleation layer 10 preferably are subjected to heat, more in particular when the 2DEG layer stack 2 is grown on the nucleation layer 10 using metalorganic chemical vapor deposition (MOCVD), causing atoms of the nucleation layer 10 to diffuse into the substrate 11.

Although this invention has been described in terms of certain embodiments, other embodiments that are apparent to those of ordinary skill in the art, including embodiments that do not provide all of the features and advantages set forth herein, are also within the scope of this invention. Moreover, the various embodiments described above can be combined to provide further embodiments. In addition, certain features shown in the context of one embodiment can be incorporated into other embodiments as well. Accordingly, the scope of the present invention is defined only by reference to the appended claims.

What is claimed is:

1. A sensor for sensing a fluidum in a space adjoining the sensor, comprising:
   a substrate;
   a two-dimensional electron gas (2DEG) layer stack formed on the substrate;
   a gate vertically interposed between the substrate and the 2DEG layer stack and laterally overlapping at least part of the 2DEG layer stack and configured to electrostatically control the electron density of a two-dimensional electron gas (2DEG) in the 2DEG layer stack; and
   a source electrode contacting the 2DEG layer stack for electrically contacting the 2DEG,
   wherein the 2DEG layer stack comprises a contact surface contacting the space and provided to contact molecules of the fluidum to be detected, and
   wherein the gate comprises a doped semiconductor bottom layer formed of a material of the substrate doped with atoms of a bottom layer of the 2DEG layer stack, wherein the doped semiconductor bottom layer is in electrical contact with at least one gate electrode extending vertically through an opening formed through the 2DEG layer stack, the doped semiconductor bottom layer being located at a side of the 2DEG layer stack opposing the contact surface.

2. The sensor of claim 1, wherein the sensor further comprises a drain electrode contacting the 2DEG layer stack for electrically contacting the 2DEG.

3. The sensor of claim 1, wherein the doped semiconductor bottom layer is doped with silicon.

4. The sensor of claim 1, wherein the 2DEG layer stack comprises a hetero-junction.

5. The sensor of claim 4, wherein the hetero-junction is formed of a GaN/AlGaN hetero-junction and the contact surface is formed on a side of a AlGaN layer of the GaN/AlGaN hetero-junction.

6. The sensor of claim 5, wherein the hetero-junction comprises a layer having the contact surface formed on a side of the layer, wherein the layer has a thickness of between about 5 nm and about 10 nm.

7. The sensor of claim 1, wherein the contact surface comprises a functionalization layer formed thereon, wherein the functionalization layer is configured to bind molecules of the fluidum to be detected.

8. The sensor of claim 7, wherein the functionalization layer comprises hemin.

9. A sensor, comprising:
   a substrate;
   a two-dimensional electron gas layer stack, comprising:
      a first semiconductor layer formed over the substrate, the first semiconductor having a first band gap, and a second semiconductor layer formed on the first semiconductor layer, the second semiconductor layer having a second band gap wider than the first band gap, wherein a heterojunction is formed at a junction formed between the first and second semiconductor layers;

a conductive back gate formed between the substrate and the first layer, wherein the heterojunction forms a two-dimensional electron gas conduction layer in response to a voltage applied to the conductive back gate; and a contact surface formed on a surface of the second semiconductor, wherein the contact surface is configured to be in contact with a fluidum and to change the conductivity of the two-dimensional electron gas conduction layer in response to the molecules of the fluidum contacting the contact surface.

10. The sensor of claim 9, further comprising a nucleation layer interposed between the first semiconductor layer and the substrate.

11. The sensor of claim 10, wherein the back gate is formed of the substrate doped with atoms of the nucleation layer.

12. The sensor of claim 11, wherein the substrate is formed of silicon.

13. The sensor of claim 10, wherein the first semiconductor layer is formed of GaN and the second semiconductor layer is formed of $Al_xGa_{1-x}N$.

14. The sensor of claim 13, wherein the nucleation layer is formed of aluminum nitride.

15. The sensor of claim 1, wherein the bottom layer of the 2DEG layer stack comprises a nucleation layer comprising AlN.

16. The sensor of claim 15, wherein the substrate comprises silicon and the bottom layer comprises silicon doped with Al atoms of the nucleation layer.

* * * * *